United States Patent [19]

Duffett et al.

[11] Patent Number: Plant 5,269

[45] Date of Patent: Aug. 7, 1984

[54] CHRYSANTHEMUM PLANT NAMED STARFIRE

[75] Inventors: William E. Duffett, Salinas, Calif.; Grace H. Mack, 108 Wahackme Rd., New Canaan, Conn. 06840

[73] Assignee: Grace H. Mack, New Canaan, Conn.

[21] Appl. No.: 435,695

[22] Filed: Oct. 21, 1982

[51] Int. Cl.[3] ..... A01H 5/00

[52] U.S. Cl. ..... Plt./77

[58] Field of Search ..... Plt./77

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum cultivar named Starfire having flat capitulum form, decorative capitulum type, white ray floret color, diameter across face of capitulum up to 75 mm., tall plant height, spreading branching pattern, average natural season flowering date of September 15, and average flowering response period of seven (7) weeks in photoperiodic controlled short day programs.

3 Drawing Figures

The present invention comprises a new and distinct cultivar of *Chrysanthemum morifolium,* Ramat., hereinafter referred to by the cultivar name Starfire.

Starfire is a product of a planned breeding program which had the objective of creating cultivars with decorative capitulum type, medium height, spreading branching pattern, durable inflorescence, seven (7) week flowering response period, and white ray floret color under outdoor natural season conditions.

Starfire was originated from a cross made by Grace H. Mack in a controlled breeding program in New Canaan, Conn. in the year 1975. The female parent was 996, white decorative, unnamed seedling from a cross of M770 × Jackpot (U.S. Plant Pat. No. 3,277). The male parent was 128, white decorative, unnamed seedling from a cross of Snowbound × Pixie Cushion (U.S. Plant Pat. No. 3,454).

Starfire was discovered and selected as a flowering plant within the progeny of the stated cross by William E. Duffett in April 1976 in a controlled greenhouse in Barberton, Ohio.

The first act of asexual reproduction of Starfire was accomplished when vegetative cuttings were taken from the initial selection in 1976 in Barberton, Ohio by William E. Duffett. Horticultural examination of selected units initiated in 1977 has demonstrated that the combination of characteristics as herein disclosed for Starfire are firmly fixed and are retained through successive generations of asexual reproduction.

Starfire has not been observed under all possible environmental conditions. The phenotype may vary significantly with variations in environment such as temperature, light intensity, and day length. The following observations, measurements, and comparisons describe plants grown in a field in Salinas, Calif.

Rooted cuttings were established in soil in one gallon containers maintained outdoors under the natural temperature and day length prevailing during July through September. Single pinching was practiced with all branches and buds retained.

The following traits have been repeatedly observed and are determined to be basic characteristics of Starfire which in combination distinguish this chrysanthemum as a new and distinct cultivar:

(1) Flat capitulum form.

(2) Decorative capitulum type.

(3) White ray floret color.

(4) Diameter across face of capitulum up to 75 mm.

(5) Tall plant height.

(6) Spreading branching pattern.

(7) Average natural season flowering date of September 15.

(8) Average flowering response period of seven (7) weeks in photoperiodic controlled flowering programs.

The accompanying photographic drawings show typical inflorescence and foliage characteristics of Starfire. Sheet 1 is a color photograph of Starfire. Sheet 2 is a black and white photograph showing three views of the inflorescence of Starfire. Sheet 3 is a black and white photograph showing the leaves of Starfire at three stages of growth (mature, intermediate, immature).

Of the many commercially available cultivars known to the present inventors, the most similar existing cultivar in comparison to Starfire is the ivory white cultivar Patriot, disclosed in U.S. Plant Pat. No. 3,897.

Reference is made to attached Chart A which compares certain characteristics of Starfire with the same characteristics of Patriot. It will be noted that in comparison to Patriot, Starfire has no ivory hue in the ray floret color, taller plant height and larger diameter across face of capitulum. The capitulum form, capitulum type, average natural season flower date, branching pattern, and plant spread of Starfire are similar to those characteristics of Patriot.

In the following description, color references are made to The Royal Horticultural Society Color Chart. The color values were determined between 10:00 and 10:30 A.M. On Sept. 15, 1981 under 150 foot-candle light intensity at Salinas, Calif.

Botanical Classification: *Chrysanthemum morifolium,* Ramat., cv Starfire.

INFLORESCENCE

A. Capitulum:

*Form.*—Flat.

*Type.*—Decorative.

*Permanence.*—3 To 4 weeks.

*Diameter across face.*—60 To 75 mm.

B. Corolla of ray florets:

*Color (abaxial).*—155D.

*Color (adaxial).*—155D.

C. Corolla of disc florets:

*Color.*—14A.

D. Reproductive organs:

*Androecium.*—Present disc florets.

*Gynoecium.*—Present both ray and disc florets.

PLANT

A. General appearance: Spreading branching pattern; tall height.

B. Foliage:

*Foliage (abaxial).*—147A.

*Foliage (adaxial).*—146A.

CHART A

COMPARISON OF STARFIRE AND PATRIOT

| CULTIVAR | RAY FLORET COLOR | CAPITULUM FORM AND TYPE | AVERAGE NATURAL SEASON FLOWER DATE |
|---|---|---|---|
| STARFIRE | WHITE | FLAT DECORATIVE | SEPTEMBER 15 |
| PATRIOT | IVORY | FLAT | SEPTEMBER 20 |

CHART A-continued

COMPARISON OF STARFIRE AND PATRIOT

| CULTIVAR | PLANT HEIGHT | WHITE DECORATIVE BRANCHING PATTERN AND SPREAD | DIAMETER ACROSS FACE OF CAPITULUM |
|---|---|---|---|
| STARFIRE | TALL | SPREADING | 60 to 75 mm. |
| PATRIOT | SHORT | COMPACT SEMI-UPRIGHT | 55 to 65 mm. |

COMPARISONS MADE OF PLANTS GROWN UNDER NATURAL SEASON OUTDOOR FIELD CONDITIONS IN SALINAS, CALIFORNIA

We claim:

1. A new and distinct cultivar of *Chrysanthemum morifolium,* Ramat., plant known by the name Starfire, as described and illustrated, and particularly characterized as to uniqueness by the combined characteristics of flat capitulum form, decorative capitulum type, durable inflorescence, white ray floret color, diameter across face of capitulum up to 75 mm., tall plant height, spreading branching pattern, average natural season flowering date of September 15, and average flowering response period of seven (7) weeks in photoperiodic controlled short day programs.

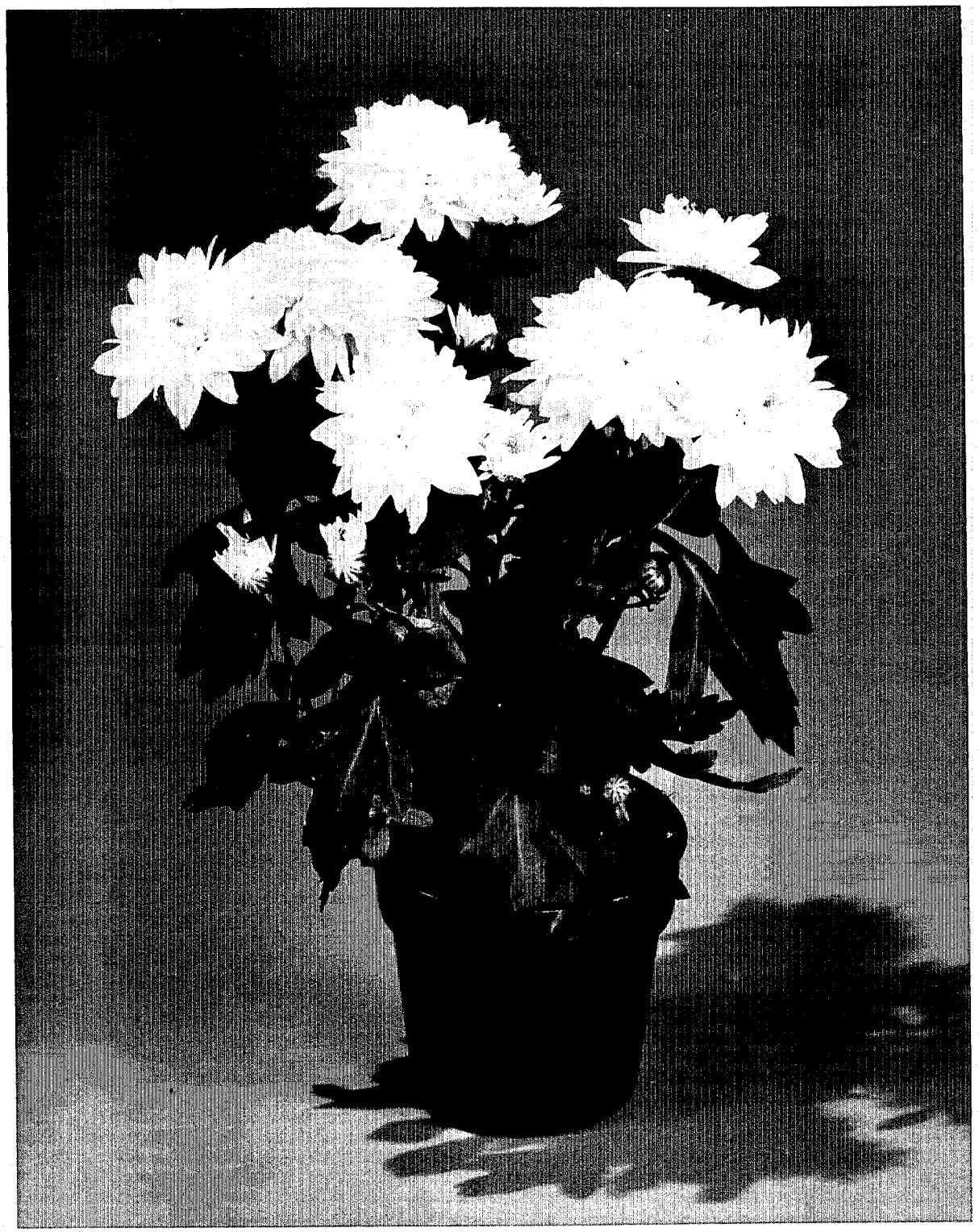

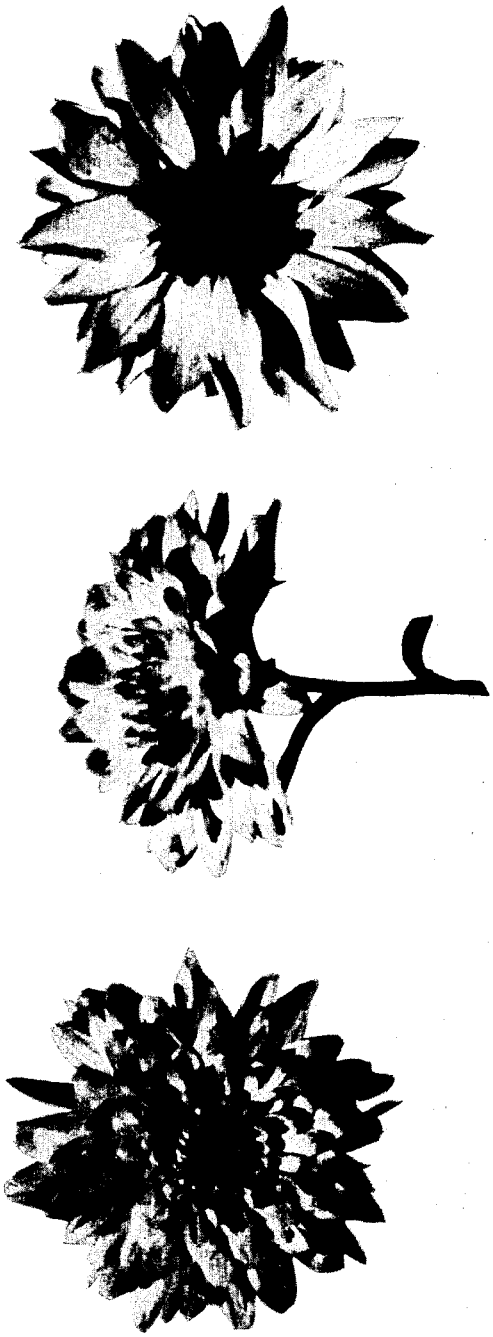

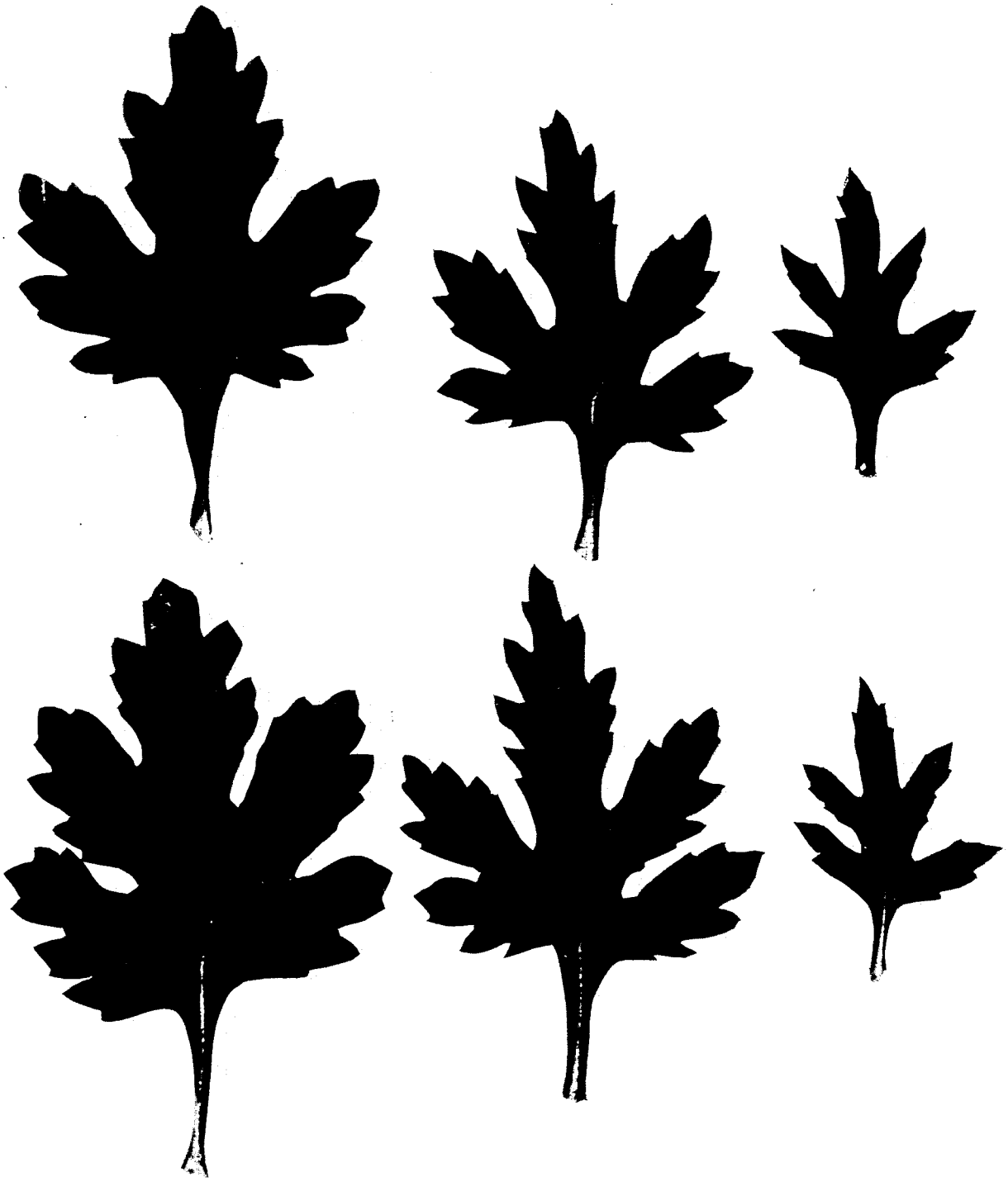

* * * * *